United States Patent [19]

Giordano et al.

[11] Patent Number: 4,734,507

[45] Date of Patent: Mar. 29, 1988

[54] OPTICALLY ACTIVE KETALS, PROCESSES FOR THEIR PREPARATION AND THEIR USE IN THE SYNTHESIS OF ALPHA-ARYLALKANOIC ACIDS

[75] Inventors: Claudio Giordano, Vicenza; Graziano Castaldi, Briona; Fulvio Uggeri, Codogno; Silvia Cavicchioli, Costermano, all of Italy

[73] Assignee: Zambon S.p.A., Vicenza, Italy

[21] Appl. No.: 720,379

[22] Filed: Apr. 5, 1985

[30] Foreign Application Priority Data

Apr. 6, 1984 [IT] Italy ................... 7204 A/84
Aug. 6, 1984 [IT] Italy ................... 7206 A/84
Aug. 6, 1984 [IT] Italy ................... 7207 A/84

[51] Int. Cl.[4] ............... C07D 317/16; C07D 317/24; C07D 317/20
[52] U.S. Cl. ................... 549/450; 549/60; 548/517; 548/527; 546/205; 546/206; 546/207; 546/213; 544/79; 544/121; 544/146; 544/148; 544/357; 544/364; 544/372; 544/374; 544/379
[58] Field of Search ............... 549/450, 60; 548/517, 548/527; 546/207, 205, 206, 213; 544/79, 121, 146, 148, 357, 364, 372, 374, 379

[56] References Cited

FOREIGN PATENT DOCUMENTS 34871 9/1981 European Pat. Off. .

*Primary Examiner*—Nicky Chan
*Attorney, Agent, or Firm*—Cushman, Darby & Cushman

[57] ABSTRACT

Compounds of formula

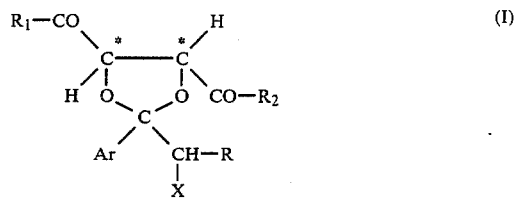

wherein
Ar represents an optionally substituted aryl group;
R represents a $C_1$–$C_4$ alkyl;
$R_1$ and $R_2$, equal to or different from each other, represent hydroxy, $O^-M^+$, $OR_3$ or

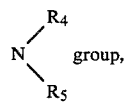

group, $R_3$ represents a $C_1$–$C_{24}$ alkyl, a $C_3$–$C_6$ cycloalkyl, a phenyl or a benzyl;
$M^+$ represents the cation of an alkaline metal;
$R_4$ and $R_5$, equal to or different from each other, represent a hydrogen atom, a $C_1$–$C_4$ alkyl, a $C_5$–$C_6$ cycloalkyl, a $(CH_2)_n$—$CH_2OH$ group with n=1, 2 or 3, or $R_4$ and $R_5$ together are a group $(CH_2)_m$ with m=4 or 5, a group —$CH_2$—$CH_2$—$R_6$—$CH_2$—$CH_2$— in which $R_6$ is an oxygen atom, an N—H or N—($C_1$–$C_4$) alkyl group;
X represents a chlorine, bromine or iodine atom, an hydroxy, acyloxy, alkylsulphonyloxy or arylsulphonyloxy group;
the carbon atoms marked by an asterisk are both contemporaneously in the R or S configuration, are described.

The preparation of the compound of formula I by ketalization or by trans-ketalization with tartaric acid derivatives and their rearrangement into alpha-arylalkanoic acids is described too.

7 Claims, No Drawings

OPTICALLY ACTIVE KETALS, PROCESSES FOR THEIR PREPARATION AND THEIR USE IN THE SYNTHESIS OF ALPHA-ARYLALKANOIC ACIDS

The present invention concerns new optically active ketals, the processes for their preparation and their use as starting products for the preparation of alpha-arylalkanoic acids.

It is well known that alpha-arylalkanoic acids represent a large class of compounds many of which are useful as anti-inflammatory and analgesic drugs.

Among these, 2-(4-isobutylphenyl)-propionic acid known as Ibuprofen, 2-(3-phenoxyphenyl)-propionic acid known as Fenoprofen, 2-(2-fluoro-4-diphenylyl)-propionic acid known as Flurbiprofen, 2-[4-(2-thienylcarbonyl)-phenyl]-propionic acid known as Suprofen, 2-(6-methoxy-2-naphtyl)-propionic acid, whose S(+) isomer is known as Naproxen, and still others may be mentioned.

Another group of alpha-arylalkanoic acids are useful as intermediates for the synthesis of pyrethroid insecticides, among which 2-(4-chlorophenyl)-3-methylbutyric acid and 2-(4-difluoromethoxyphenyl)-3-methylbutyric acid may be mentioned.

Many alpha-arylalkanoic acids have at least an asymmetry center, on the carbon atom in alpha to the carboxyl, and they exist consequently in the form of stereoisomers. Often, to one of the isomers (enantiomers) a definitely higher biological activity is associated.

A particularly evident example is given by 2-(6-methoxy-2-naphthyl)-propionic acid, whose S(+) enantiomer (Naproxen) has definitely higher pharmacological properties than the R(−) enantiomer, and than the racemic mixture.

Among the processes for the preparation of alpha-arylalkanoic acids recently described the most interesting are those which comprise the rearrangement of alkyl-aryl-ketals substituted in the alpha position with respect to the ketal group.

The processes described in European patent applications No. 34871 (Blaschim), No. 35305 (Blaschim), No. 48136 (Sagami), No. 64394 (Syntex), No. 89711 (Blaschim), No. 101124 (Zambon), in Italian patent applications No. 21841 A/82 (Blaschim and CNR), No. 22760 A/82 (Zambon) and No. 19438 A/84 (Zambon) and in the paper J. Chem. Soc. Perkin I, 11, 2575 (1982) may be cited.

All these processes afford, more or less conveniently, alpha-arylalkanoic acids in the form of racemic mixture.

The preparation of optically active alpha-arylalkanoic acids may be carried out by resolution of the racemic mixtures thus obtained according to conventional procedures, e.g. with optically active bases, or by carrying out the above mentioned rearrangement process on optically active ketals previously prepared according to procedures described in European patent applications No. 67698 (Sagami) and No. 81993 (Syntex).

All the above cited processes use as the starting material for the preparation of alpha-arylalkanoic acids, ketals obtained by reacting aryl-alkyl-ketones with aliphatic alcohols or glycols. We have now found, and they are an object of the present invention, new chiral, enantiomerically pure ketals of aryl-alkyl-ketones having in the ketal group two asymmetric centers both in the R or S configuration, which are useful as intermediates for the preparation of optically active alpha-arylalkanoic acids or their precursors either with equivalent or enhanced optical purity with respect to the starting ketals.

The new ketals according to the invention have the formula:

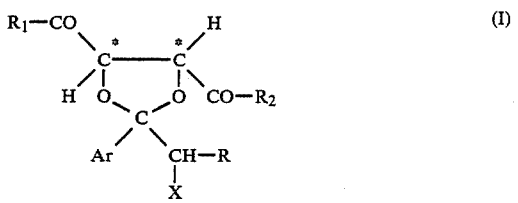

wherein
Ar represents an optionally substituted aryl group;
R represents a $C_1$-$C_4$ alkyl;
$R_1$ and $R_2$, equal to or different from each other, represent hydroxy, $O^-M^+$, $OR_3$ or

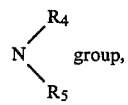

group, $R_3$ represents a $C_1$-$C_{24}$ alkyl, a $C_3$-$C_6$ cycloalkyl, a phenyl or a benzyl;
$M^+$ represents the cation of an alkaline metal;
$R_4$ and $R_5$, equal to or different from each other, represent a hydrogen atom, $C_1$-$C_4$ alkyl, $C_5$-$C_6$ cycloalkyl, $(CH_2)_n$—$CH_2OH$ group with n=1, 2 or 3, or $R_4$ and $R_5$ together are a group $(CH_2)_m$ with m=4 or 5, a group —$CH_2$—$CH_2$—$R_6$—$CH_2$—$CH_2$— in which $R_6$ is an oxygen atom, N—H or N—($C_1$-$C_4$) alkyl group;
X represents a chlorine, bromine or iodine atom, a hydroxy, acyloxy, alkylsulphonyloxy or arylsulphonyloxy group;
the carbon atoms marked with an asterisk are both contemporaneously in the R or S configuration.

The compounds of formula I in which X is different from hydroxy are useful for the preparation of alpha-arylalkanoic acids by rearrangement and such rearrangement process is a second object of the present invention.

Aryl, in formula I, may preferably be an aromatic monocyclic, polycyclic, orthocondensed polycyclic or heteroaromatic group having up to 12 carbon atoms in the aromatic ring such as e.g. phenyl, diphenyl, naphtyl, thienyl and pyrrolyl.

The optional substituents of said aryls groups comprise one or more halogen atoms, $C_1$-$C_4$ alkyl, $C_3$-$C_6$ cycloalkyl, benzyl, hydroxy, $C_1$-$C_4$ alkoxy, $C_1$-$C_4$ alkylthio, $C_1$-$C_4$ haloalkyl, $C_1$-$C_4$ haloalkoxy, phenoxy, thienylcarbonyl and benzoyl substituents.

Specific examples of Ar include: 4-isobutyl-phenyl, 3-phenoxy-phenyl, 2-fluoro-4-diphenyl, 4'-fluoro-4-diphenyl, 4-(2-thienylcarbonyl)-phenyl, 6-methoxy-2-naphthyl, 5-chloro-6-methoxy-2-naphthyl, 5-bromo-6-methoxy-2-naphthyl, 4-chlorophenyl, 4-difluoromethoxy-phenyl, 6-hydroxy-2-naphthyl, 5-bromo-6-hydroxy-2-naphthyl, and 5-chloro-6-hydroxy-2-naphthyl.

When X=acyloxy in formula I specifically comprises acetoxy, trichloroacetoxy, trifluoroacetoxy, benzoyloxy, 4-nitro-benzoyloxy and in general, an acyloxy group which is a good leaving group; alkylsulphonyloxy and arylsulphonyloxy represent a group of formula $$-O-SO_2-R_7$$

wherein $R_7$ preferably represents a $C_1-C_4$ alkyl or a $C_6-C_{20}$ alkyl-aryl groups; specific examples are mesylate, benzensulphonate and tosylate.

The preparation of the compounds of formula I, and this is a further object of the present invention, is carried out according to one of the following alternative procedures.

(a) Ketalization of a ketone of formula $$Ar-CO-\underset{X}{\underset{|}{CH}}-R \quad (II)$$

wherein Ar, R and X have the above reported meanings, with L(+)-tartaric acid or D(−)-tartaric acid or a derivative thereof of formula $$R_1-CO-\overset{*}{\underset{OH}{\underset{|}{CH}}}-\overset{*}{\underset{OH}{\underset{|}{CH}}}-CO-R_2$$

wherein $R_1$ and $R_2$ have the above reported meanings.

The ketalization reaction is carried out by heating in the presence of an acid catalyst and of an orthoester; alternatively the water formed in the ketalization is azeotropically distilled off in the presence of a suitable organic solvent such as benzene, toluene, xylene or heptane.

This preparation process is particularly suitable for obtaining the ketals of formula I in which $R_1$ and $R_2$, equal to or different from each other, represent an $OR_3$ group. Starting from said ketals it is possible to prepare all the ketals in which $R_1$ and $R_2$ have the above reported meanings.

For example, the partial hydrolysis with one equivalent of a base (e.g. an alkaline hydroxide) of the ketals of formula I in which $R_1=R_2=OR_3$ affords the corresponding mono-salts (e.g. $R_1=O^-M^+$, $R_2=OR_3$); from these latters the corresponding mono-acids (e.g. $R_1=OH$, $R_2=OR_3$) are prepared by acidification. The hydrolysis of the ketals in which $R_1=R_2=OR_3$ with two equivalents of a base (e.g. an alkaline hydroxide) affords the corresponding salts (e.g. $R_1=R_2=O^-M^+$) which by acidification provide the corresponding dicarboxylic derivatives ($R_1=R_2=OH$). These latters may be easily transformed into other derivatives such as esters (e.g. $R_1$ and/or $R_2=OR_3$) or amides.

The amide-derivatives may also be directly prepared from the ketals of formula I in which $R_1=R_2=OR_3$ by reaction with the suitable amine of formula $R_4R_5N-H$.

By direct ketalization it is also possible to prepare ketals of formula I in which the substituent X has a meaning different from that of the starting ketone (II).

Thus, starting from a ketone of formula II in which X is a chlorine or bromine atom, it is possible to obtain a ketal of formula I in which X=OH by treating with a strong base such as an alkaline alcoholate.

The ketals of formula I in which X is an acyloxy, alkylsulphonyloxy or arylsulphonyloxy group can be prepared by reacting the ketals of formula I in which X is hydroxy with the suitable acyl, alkylsulphonyl or arylsulphonyl halide. If desired, from the ketals of formula I in which X is an acyloxy group it is possible to prepare by hydrolysis the ketals of formula I in which X is hydroxy.

(b) Transketalization of a ketal of formula

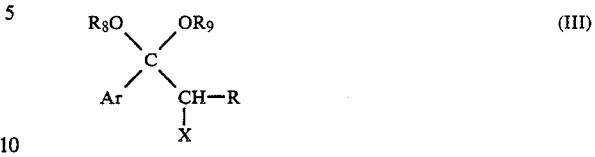

in which Ar, R and X have the above reported meanings, $R_8$ and $R_9$ represent a $C_1-C_6$ alkyl group or $R_8$ and $R_9$ together represent a $C_2-C_6$ alkylene radical so as to form a 5 or 6-membered ring together with the O—C—O group.

The transketalization reaction is carried out by heating at a temperature from 20° to 100° C. in an inert gas atmosphere, a mixture of a ketal of formula III and L(+)- or D(−)-tartaric acid or a derivative thereof, in the presence of an acid catalyst under anhydrous conditions.

Suitable acidic catalysts are mineral or sulphonic acids.

Also in this case, it is possible to modify the meanings of $R_1$, $R_2$ and X according to that described under paragraph (a). Both the ketone of formula II and the ketals of formula III are known compounds, easily prepared according to known procedures. It is worth noting that the carbon atoms marked by an asterisk in the ketals of formula I, independently from the method of preparation, have the same configuration of the starting tartaric acid, i.e. they are both in the R or in the S configuration.

We have quite surprisingly found that the reactions for the preparation of the ketals of formula I according to the method (a) as well as to the method (b) hereabove are diastereogenic and, depending on the reaction conditions, they may also be stereoselective in the sense that they afford a mixture of ketals of formula I in which one of the two epimers (with respect to the carbon atom bonded to the X group) is prevailing or strongly prevailing. By selecting the suitable ketone of formula II and the suitable tartaric acid derivative it is possible to obtain essentially the desired optically active epimer.

It is evident that starting from an already optically active ketone of formula II it is possible to obtain epimeric ketals of formula I in which the ratio between the two epimers is higher than that of the enantiomers in the starting ketones.

Independently from that hereabove reported, it is also important the fact that the ketals of formula I exist in the form of epimers which can be easily enriched or separated according to known procedure, for example by crystallization.

It is thus possible to separate the desired epimer of the ketal of formula I and to rearrange it to obtain the corresponding optically active alpha-arylalkanoic acid in a substantially pure form. An isomer separation carried out on a precursor i.e. an intermediate compound is very often more convenient than the separation (resolution) of the final product because of the lower cost of the intermediate.

The possibility of preparing ketals of formula I containing a variety of different groups, with reference to the $R_1$ and $R_2$ substituents, allows to modulate in a wide range the hydrophilic and lipophilic character of said ketals: from compounds having strong polar groups (alkaline salts, amides) to lipophilic compounds (esters of long chain alcohols).

This wide choice allows to select the best suited ketal of formula I with respect to the experimental conditions used in the different processes for the preparation of alpha-arylalkanoic acids by rearrangement.

It is worth noting that tartaric acid derivatives, and in particular L(+)-tartaric acid have a price on the market which is competitive with that of the glycols up to now used for ketalization according to the above cited known rearrangement processes. The preparation of alpha-arylalkanoic acids by rearrangement of the ketals of formula I may be carried out by using experimental procedures known for other different ketals, in one stage or in two stages.

We have also found that such processes when applied to the ketals of formula I (in which X is different from hydroxy) provide alpha-arylalkanoic acids in which the enantiomeric ratio reflects the epimeric ratio of the starting ketals.

The rearrangement process to be selected depends on the nature of the starting ketal and particularly on the specific substituent X present on the ketal itself.

For example, the ketals of formula I in which X is a iodine atom, when Ar is the 6-methoxy-2-naphthyl group and R is $CH_3$ may be conveniently rearranged by using the procedures described in European patent application No. 89711 or in Italian patent application No. 21841 A/82.

The ketals in which X is a halogen atom and Ar is any of the aryl groups may be rearranged in the presence of certain metal salts as catalyst according to the procedures described in European patent application No. 34871 or No. 35305 and in the paper J. Chem. Soc. Perkin I, 11, 2575 (1982); alternatively their rearrangement may be carried out in a polar protic medium in neutral or slightly alkaline conditions, optionally in the presence of an inert diluent according to the procedure described in Italian patent application No. 22760 A/82 or in European patent application No. 101124.

Among said procedures, the latter is preferred because it is easier to be carried out and because it does not require metal salts as catalysts.

The ketals of formula I in which X is a good leaving group such as acyloxy, alkylsulphonyloxy or arylsulphonyloxy may be converted into derivatives of alpha-arylalkanoic acids following the procedure described in European patent application No. 48136.

All the above cited rearrangement procedures generally provide alpha-arylalkanoic acids in the form of derivatives thereof in particular in the form of esters. These are then hydrolyzed to the corresponding acids according to known methods.

We have also found, and this is a further object of the present invention, a new rearrangement process which leads to alpha-arylalkanoic acids having an enantiomeric ratio higher than the epimeric ratio of the starting ketals.

Such a process is defined herewith as enantioselective in that the enantiomeric composition (ratio between enantiomers S and R) of the thus obtained alpha-arylalkanoic differs from the epimeric composition of the starting ketals of formula I and quite surprisingly corresponds to an increase in the optical purity of the alpha-arylalkanoic acids.

The enantioselective rearrangement process object of the present invention consists in treating a ketal of formula I in which X is different from hydroxy in aqueous medium, at an acid pH, at a temperature comprised between room temperature and 150° C.

The above mentioned reaction conditions are particularly unexpected and surprising in that it is well known that the treatment of a ketal with water under acidic conditions is a general method to convert it into the corresponding ketone and alcohol or diol. Accordingly, the previously known alpha-substituted alkyl-aryl-ketals in such conditions undergo a fast hydrolysis providing the corresponding alkyl-aryl-ketone and alcohol or diol.

The new rearrangement process object of the invention is preferably carried out by using ketals of formula I soluble or at least partially soluble in water under the reaction conditions, i.e. the ketals of formula I in which $R_1$ and/or $R_2$ are hydrophilic groups. Depending on the nature of the ketal of formula I a co-solvent may be used.

The rearrangement is preferably carried out by heating the ketal of formula I in water at pH comprised between 4 and 6.

The desired pH values may be maintained by adding a suitable amount of a buffer.

The reaction duration depends mainly on the nature of the ketal of formula I, and on the reaction temperature.

Usually, the alpha-arylalkanoic acids are scarcely soluble in water, therefore at the end of the reaction the optically active alpha-arylalkanoic acid may be isolated by simple filtration. As far as we know, this is the first time that a rearrangement of ketals for the preparation of alpha-arylalkanoic acids is carried out in water essentially as the only reaction solvent.

The main advantages of the present rearrangement process from an industrial point of view, may be summarized as follows: (1) the process is enantioselective and provides alpha-arylalkanoic acids with an enantiomeric ratio higher than the epimeric ratio of the starting material; (2) the reaction solvent is water with the consequent economic and safety advantages; (3) no metal catalyst is required and (4) the optically active alpha-arylalkanoic acid is separated from the reaction mixture by filtration.

Among the optically active alpha-arylalkanoic acids the most important from a pharmaceutical point of view is 2-(6-methoxy-2-naphthyl)-propionic acid whose S(+) enantiomer is generally known as Naproxen.

In a specific form of realization the present invention concerns the ketals of formula IV

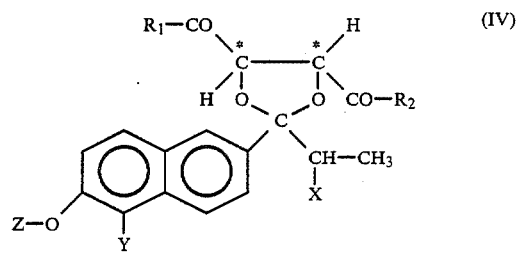

wherein $R_1$, $R_2$ and X have the same meanings as those reported for formula I, Y represents a hydrogen, chlorine or bromine atom, Z represents a hydrogen atom, a methyl or an alkaline metal, and their use in the preparation of Naproxen by rearrangement.

A preferred embodiment in the synthesis of Naproxen according to the present invention consists of the rearrangement of a ketal of formula IV in which Z is methyl and X is a halogen atom in a polar solvent in neutral or slightly alkaline conditions.

An alternative preferred rearrangement procedure consists in treating a compound of formula IV in which Z represents an alkaline metal in water or in an organic solvent, under basic conditions.

The ketals of formula IV in which X is an acyloxy, alkylsulphonyloxy or arylsulphonyloxy group may be rearranged in a protic medium, under neutral or basic conditions.

In any case, the preferred rearrangement procedure of the ketals of formula IV in which X is different from hydroxy is the enantioselective process in aqueous medium, under acidic conditions according to the invention.

In order to prepare Naproxen it may be necessary to replace the substituent Y (when this is a chlorine or bromine atom) by a hydrogen atom. This is accomplished by hydrogenolysis of the corresponding 2-(5-chloro or 5-bromo-6-methoxy-2-naphthyl)-propionic acid or esters thereof.

As already stated hereinbefore, the rearrangement of the ketals of formula I to alpha-arylalkanoic acids is a process which does not lead to substantial racemization of the products and thus selectively and prevailingly provides the desired optically active alpha-arylalkanoic acids.

The rearrangement reaction of the compounds of formula I, in particular when carried out under mild conditions, in organic medium, in the absence of alcohols or glycols, may give rise to the formation of new intermediate esters of formula

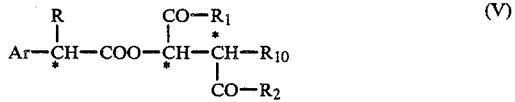

wherein Ar, R, $R_1$ and $R_2$ have the same meanings as those given for formula I and $R_{10}$ is a hydroxy or a chlorine, bromine or iodine atom. Depending on the reaction conditions $R_{10}$ may also have other meanings such as acetate, propionate, benzoate.

Hydrolysis of the compound of formula V, carried out preferably under acidic conditions, provides the corresponding free acids.

Accordingly, the rearrangement of the compounds of formula IV when carried out under mild conditions, in organic medium, in the absence of alcohols or glycols, may give rise to new esters of formula

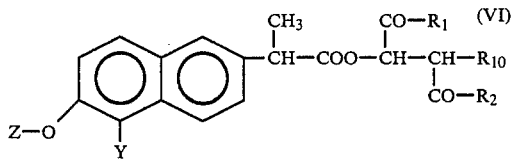

wherein Y, Z, $R_1$, $R_2$ and $R_{10}$ have the above reported meanings.

Hydrolysis of the esters of formula VI, preferably in acidic conditions according to the invention, provides Naproxen or a precursor thereof. Also in this case in which the preparation of alpha-arylalkanoic acids is achieved in two stages throught the esters of formula V or VI, no substantial racemization occurs and the obtained alpha-arylalkanoic acid consists of a mixture in which one of the enantiomers prevails.

The compounds of formula V and VI are new compounds endowed with interesting characteristics because of which they are useful in many respects.

As already mentioned they furnish by hydrolysis the corresponding alpha-arylalkanoic acids.

Moreover, thanks to the presence of two asymmetric centers (the carbon atoms to which the groups CO—$R_1$ and CO—$R_2$ are bonded) in the alcoholic moiety, they are useful for the optical resolution of alpha-arylalkanoic acids.

The resolution of an acid into its optical isomers is generally carried out by the formation of a salt with an optically active base.

By using the compounds of formula V or VI a new resolution process is realized for the separation of optically active alpha-arylalkanoic acids. Such resolution which does not comprise the preparation of a salt with an optically active base but comprises formation of an ester with tartaric acid or a derivative thereof in quite new. Said resolution process is particularly advantageous when the rearrangement of the ketals of formula I provides a mixture of esters of formula V enriched in the desired optical isomer is obtained.

Nevertheless, it is clear that the compounds of formula V and VI are useful for the resolution of alpha-arylalkanoic acids independently from how they have been prepared.

In fact, it is possible to prepare the compounds of formula V or VI by esterification, with tartaric acid or a derivative thereof, of a racemic mixture (or of a mixture rich in one of the optical isomers) of an alpha-arylalkanoic acid prepared according to any procedure.

The presence of a chiral group in the alcoholic moiety is also the key for obtaining, starting from a mixture of esters, under alkaline conditions the equilibrium of the mixture from which the desired isomer can be isolated by crystallization.

According to a specific embodiment of the present invention the esters of formula VI, when prepared by rearrangement of a ketal of formula IV as well as when prepared by reacting a racemic 2-(6-methoxy-2-naphthyl)-propionic acid or a precursor thereof with tartaric acid or a derivative thereof, may be used in a process for the resolution of Naproxen or a precursor thereof by fractional crystallization of the ester of formula VI whose hydrolysis provides Naproxen or a precursor thereof in a substantially pure form.

Said ester is the ester of S(+)-2-(6-methoxy-2-naphthyl)-propionic acid (or a precursor thereof such as 5-chloro or 5-bromo-derivative) with the naturally occurring L(+)-tartaric acid (or a derivative thereof such as an ester or amide).

A further unexpected characteristic of the esters of formula V or VI consists in the fact that they are per se pharmacologically active.

Particularly interesting are the compounds of formula VI.

In the following tables are reported the results of the tests for anti-inflammatory and anti-piretic activity of the compounds of formula VI in which:
(compound a) $R_1=R_2=OCH_3$, $R_{10}=OH$, $Y=H$, $Z=CH_3$;
(compound b) $R_1=R_2=OCH_3$, $R_{10}=OH$, $Y=Br$, $Z=CH_3$;

with respect to Naproxen and 5-bromo-Naproxen (compound c).

From these results it is evident that the new compounds, although having an activity lower than that of Naproxen, are nevertheless endowed with an interesting pharmacological activity which could also find a practical application in human therapy.

TABLE 1

Antiinflammatory activity of compounds (a) and (b) with respect to Naproxen and 5-bromo-Naproxen (c) by oral administration.

| Compound | Dose μM/kg/os | Inhibition (3rd hour) (%) | $ED_{50}$ (C.L. 95%) |
|---|---|---|---|
| (a) | 10 | 0 | 175 |
|  | 30 | 0 | (110–280) |
|  | 100 | 16 |  |
| (b) | 10 | 3 | 160 |
|  | 30 | 14 | (100–250) |
|  | 100 | 20 |  |
| (c) | 10 | 6 |  |
|  | 30 | 34 |  |
|  | 100 | 34 | 196 |
|  | 300 | 56 | (120–304) |
| Naproxen | 10 | 38 |  |
|  | 30 | 45 | 31 |
|  | 100 | 66 | (19–49) |

TABLE 2

Anti-piretic activity of compound (a) and (b) with respect to Naproxen and 5-bromo-Naproxen (c) by oral administration in rats.

| Compound | Dose μM/kg/os | Variation in the body temperature (°C.) after | |
|---|---|---|---|
|  |  | 1 hour | 2 hours |
| (a) | 10 | −0.02 | +0.02 |
|  | 30 | +0.07 | −0.61 |
|  | 100 | +0.01 | +0.76 |
|  | 300 | +0.03 | −0.81 |
| (b) | 10 | −0.17 | −0.19 |
|  | 30 | −0.49 | −0.68 |
|  | 100 | −0.46 | −0.68 |
| (c) | 30 | −0.17 | −0.66 |
|  | 100 | −1.33 | −1.67 |
|  | 300 | −1.42 | −1.84 |
| Naproxen | 3 | −0.38 | −0.52 |
|  | 10 | −1.22 | −1.48 |
|  | 30 | −1.86 | −1.89 |

TABLE 3

Anti-pyretic activity of compounds (a) and (b) with respect to Naproxen and 5-bromo-Naproxen (c) by intraperitoneal administration in rats.

| Compound | Dose μM/kg/ip | Variation in the body temperature (°C.) after | | |
|---|---|---|---|---|
|  |  | 30 min | 1 hour | 4 hours |
| (a) | 10 | −0.26 | −0.52 | −0.19 |
|  | 30 | −0.61 | −1.02 | −0.56 |
| (b) | 10 | −0.24 | −0.52 | −0.26 |
|  | 30 | −0.77 | −0.87 | −0.44 |
| (c) | 30 | −0.55 | −1.01 | +0.06 |
|  | 100 | −0.78 | −1.45 | −0.99 |
| Naproxen | 10 | −1.00 | −1.10 | −0.86 |

With the scope to better illustrate the invention without however limiting it in any way, a set of examples is given in the following.

EXAMPLE 1

Ketalization of
2-bromo-1-(6-methoxy-2-naphthyl)-propan-1-one with
2(R),3(R)-dihydroxy-butanedioic acid dimethyl ester
(L(+)-dimethyl tartrate)

A mixture of 2-bromo-1-(6-methoxy-2-naphthyl)-propan-1-one (1.465 g, 0.005 mol), L(+)-dimethyltartrate (7.5 g), trimethyl orthoformate (2.5 g, 0.0236 mol) and trifluoromethanesulfonic acid (0.075 g, 0.0005 mol) was kept, under stirring and under nitrogen, at 50° C. for 60 hours. The reaction mixture was poured into a 10% aqueous solution of sodium carbonate and extracted with dichloromethane. The organic phase was washed with water and dried over sodium sulphate. Evaporation of the solvent under reduced pressure gave a crude that was purified by column chromatography (silica gel; eluent hexane:diethylether=8:2).

The mixture of the two diastereoisomers of 2-(1-bromoethyl)-2-(6-methoxy-2-naphthyl)-1,3-dioxolane-4(R),5(R)-dicarboxylic acid dimethyl ester 1 and 2 (0.9 g, 0.002 mol) in ratio 1:2=1:1 (determined by $^1$H-NMR 200 MHz) was obtained.

Diastereoisomer 1 (RRS)
$^1$H-NMR (200 MHz, CDCl$_3$-TMS), delta (ppm): 1.68(d, 3H, J=7.5 Hz); 3.54(s, 3H); 3.90(s, 3H); 4.08(s, 3H); 4.48(q, 1H, J=7.5 Hz); 4.94(2H, ABq, Δγ=26.8, J=7.2 Hz); 7.1–8.0(6H, aromatic protons).

Diastereoisomer 2 (RRR)
$^1$H-NMR (200 MHz, CDCl$_3$-TMS), delta (ppm): 1.64(d, 3H, J=7.5 Hz); 3.58(s, 3H); 3.89(s, 3H); 4.08(s, 3H); 4.50(q, 1H, J=7.5 Hz); 4.89(2H, ABq, Δγ=36.3, J=6.3 Hz); 7.1–8.0(6H, aromatic protons).

EXAMPLE 2

Preparation of the diastereoisomeric mixture of
2-(1-bromoethyl)-2-(6-methoxy-2-naphthyl)-1,3-dioxolane-4(R),5(R)-dicarboxylic acid in ratio 1:1

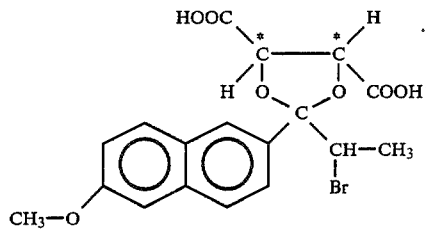

A mixture of the two diastereoisomers of 2-(1-bromoethyl)-2-(6-methoxy-2-naphthyl)-1,3-dioxolane-4(R),5(R)-dicarboxylic acid diethyl ester 3 and 4 (prepared in a similar manner as described in the example 1) (21.18 g, 0.044 mol, ratio 3:4=1:1), sodium hydroxide (3.52 g, 0.088 mol), dimethoxyethane (35 ml) and of water (35 ml) was kept, under stirring, at room temperature for 2 hours. The reaction mixture was diluted with water and extracted with diethylether. The aqueous phase was acidified with concentrated hydrochloric acid to pH 1 and extracted with diethylether. The organic phase was washed with water and dried over sodium sulphate. Evaporation of the solvent under reduced pressure gave the two diastereoisomers of 2-(1-bromoethyl)-2-(6-methoxy-2-naphthyl)-1,3-dioxolane-4(R),5(R)-dicarboxylic acid 5 and 6 (16 g, 0.0367 mol; yield 85.5%) in ratio 5:6=1:1 (determined by $^1$H-NMR 200 MHz).

A sample, obtained by esterification in diethylether with diazomethane, gave a mixture of the two diastereoisomers of 2-(1-bromoethyl)-2-(6-methoxy-2-naphthyl)-1,3-dioxolane-4(R),5(R)-dicarboxylic acid dimethyl ester 1 and 2 in ratio 1:2=1:1 (determined by HPLC and by $^1$H-NMR 200 MHz).

EXAMPLE 3

Preparation of 2-(1-chloroethyl)-2-(6-methoxy-2-naphthyl)-1,3-dioxolane-4(R),5(R)-dicarboxilic acid dimethyl ester A mixture of 2-chloro-1-(6-methoxy-2-naphthyl)-propan-1-one (12.4 g, 0.05 mol), 2(R),3(R)-dihydroxy butanedioic acid dimethyl ester (75 g) and trimethyl orthoformate (25 g, 0.236 mol) was gradually heated up to 50° C.

Trifluormethanesulfonic acid (2.4 g, 0.016 mol) was added to the solution. The reaction mixture was kept, under nitrogen, at 50° C. for 45 hours; then it was worked up as described in example 1. Purification of the crude (19.2 g), so obtained, by column chromatography (silica gel; eluent hexane:diethylether=6:4) gave the mixture of the desired diastereoisomers 7 and 8 (5.6 g) in ratio 7:8=52:48 (determined by HPLC).

$^1$H-NMR (200 MHz, CDCl$_3$-TMS): Diastereoisomer 7 (RRS) delta (ppm): 1.49(d, 3H, J=6.65 Hz); 3.48(s, 3H); 3.85(s, 3H); 3.89(s, 3H); 4.41(q, 1H, J=6.65 Hz); 4.95(ABq, 2H, J=6 Hz); 7.1–8.0(6H, aromatic protons).

Diastereoisomer 8 (RRR) delta (ppm): 1.47(d, 3H, J=6.65 Hz); 3.53(s, 3H); 3.83(s, 3H); 3.89(s, 3H); 4.44(q, 1H, J=6.65 Hz); 4.92(ABq, 2H, J=6 Hz); 7.1–8.0(6H, aromatic protons).

HPLC analysis was performed on a Hewlett Packard instrument (mod. 1084/B with a variable wavelength UV detector):
column: Brownlee Labs RP8 (5 micron) spheri 250 mm×4.6 mm
solvent A: water, flow 0.96 ml/min
solvent B: methanol, flow 1.04 ml/min
temperature solvent A: 60° C.
temperature solvent B: 40° C.
column temperature: 50° C.
wavelength: 254 nm
injection: 10 microliters of a 3 mg/ml solution in acetonitrile retention times:
diastereoisomer 7: 12,46 min
diastereoisomer 8: 13.21 min

EXAMPLE 4

Preparation of 2(R)-hydroxy-3(R)-[2-(6-methoxy-2-naphthyl)-propanonyl]-butanedioic acid dimethyl ester

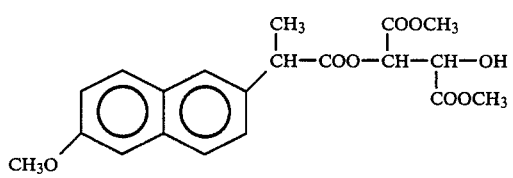

A solution of silver tetrafluoroborate (2.4 g, 0.0123 mol) in 1,2-dichloroethane (8 ml) was added, under inert atmosphere, in 15 minutes to a solution of the two diastereoisomers 7 and 8 (4.09 g, 0.01 mol) in ratio 7:8=52:48 kept under stirring at 15° C. The reaction mixture was heated at 50° C., kept at 50° C. for 16 hours, then cooled at room temperature and filtered.

The solution was diluted with dichloromethane (60 ml), washed with water (2×100 ml) and dried over sodium sulphate. Evaporation of the solvent under reduced pressure gave a crude that after purification by column chromatography (silica gel; eluent n-heptane:diethylether=2:8) led to the mixture of two diastereoisomeric esters A and B (2.9 g, 0.0074 mol; yield 74%) in ratio A:B=52:48 (determined by $^1$H-NMR 200 MHz).

$^1$H-NMR (200 MHz, CDCl$_3$-TMS), delta (ppm): Diastereoisomer A (RRS): 1.62(d, 3H, J=8 Hz); 3.22(s, 3H); 3.83(s, 3H); 3.92(s, 3H); 3.21(d, 1H, J=7.2 Hz); 3.95(q, 1H, J=8 Hz); 4.68(dd, 1H, J=$_{CH\text{-}OH}$=7.2 Hz, J$_{CH\text{-}CH}$=2.47 Hz); 5.37(d, 1H, J=2.47 Hz); 7.1–7.8(6H, aromatic protons).

Diastereoisomer B (RRR): 1.66(d, 3H, J=8 Hz); 3.58(s, 3H); 3.72(s, 3H); 3.92(s, 3H); 3.24(d, 1H, J=7.6 Hz); 3.97(q, 1H, J=8 Hz); 4.78(dd, 1H, J$_{CH\text{-}OH}$=7.6 Hz, J$_{CH\text{-}CH}$=2.47 Hz); 5.45(d, 1H, J=2.47 Hz); 7.1–7.8(6H, aromatic protons).

EXAMPLE 5

Preparation of 2-(6-methoxy-2-naphthyl)-propanoic acid

A mixture of the two diastereoisomeric esters A and B (2.2 g, 5.64 mmol; in ratio A:B=52:48, prepared as described in example 4), 1,2-dimethoxyethane (22 ml) and of concentrated hydrochloric acid (22 ml) was kept at 95° C. for 2 hours. The reaction mixture was cooled at room temperature, diluted with water and extracted with dichloromethane. The organic phase was washed with water and extracted with a 10% aqueous solution of sodium bicarbonate.

The basic aqueous phase was acidified with concentrated hydrochloric acid and extracted with dichloromethane. The organic phase was washed with water and dried over sodium sulphate. Evaporation of the solvent under reduced pressure gave the crude 2-(6-methoxy-2-naphthyl)-propanoic acid. An analytically pure sample was obtained after purification by column chromatography (silica gel; eluent hexane:diethylether=7:3).

$[\alpha]_D^{20}$= +2.2° (c=1%, chloroform)

EXAMPLE 6

Preparation of 2-(1-chloroethyl)-2-(6-methoxy-2-naphthyl)-1,3-dioxolane-4(R),5(R)-dicarboxylic acid Following the procedure described in example 2, starting from a mixture of the two diastereoisomers of 2-(1-chloroethyl)-2-(6-methoxy-2-naphthyl)-1,3-dioxolane-4(R),5(R)-dicarboxylic acid dimethyl ester (38.4 g, 0.094 mol; in ratio 7:8=1:1, determined by HPLC) a mixture of the two diastereoisomers of the desired product 9 and 10 (32.5 g, 0.085 mol; 90.0%) yield in ratio 9:10=1:1, was obtained.

The diastereoisomeric ratio was determined by HPLC analysis carried out on a sample obtained by esterification with diazomethane.

$^1$H-NMR (CDCl$_3$-TMS), delta (ppm), significative data: Diastereoisomer 9: 1.44(d, 3H, J=6.85 Hz); 4.42(q, 1H, J=6.85 Hz); 4.88(ABq, 2H, J=6 Hz); 7.0–8.0(6H, aromatic protons); 9.0(s, 2H).

Diastereoisomer 10: 1.44(d, 3H, J=6.85 Hz); 4.42(q, 1H, J=6.85 Hz); 4.82(ABq, 2H, J=6.7 Hz); 7.0–8.0(6H, aromatic protons); 9.0(s, 2H).

EXAMPLE 7

Preparation of 2-(1-bromoethyl)-2-(5-bromo-6-methoxy-2-naphthyl)-1,3-dioxolane-4(R),5(R)-dicarboxylic acid diethyl ester A solution of bromine (13.42 g, 0.084 mol) in carbon tetrachloride (30 ml) was added dropwise, during 1 hour, to a solution of the two diastereoisomers of 2-(1-bromoethyl)-2-(6-methoxy-2-naphthyl)-1,3-dioxolane-4(R),5(R)-dicarboxylic acid diethyl ester 3 and 4 in ratio 3:4=1:1 (39.48 g, 0.082 mol) in carbon tetrachloride (457 ml), kept under stirring at 0° C. and under inert atmosphere. The reaction mixture was kept at 0° C. for 1 hour; then it was poured to a well stirred 10% aqueous solution of sodium carbonate (500 ml). The organic phase was separated, washed with water (2×500 ml) and dried over sodium sulphate. Evaporation of the solvent under reduced pressure gave the diastereoisomeric mixture of 2-(1-bromoethyl)-2-(5-bromo6-methoxy-2-naphthyl)-1,3-dioxolane-4(R),5(R)-dicarboxylic acid diethyl ester 11 and 12 (43.6 g; purity 98% and ratio 11:12=1:1, determined by HPLC).

EXAMPLE 8

Preparation of the diastereoisomeric mixture of 2-(1-bromoethyl)-2-(6-methoxy-2-naphthyl)-1,3-dioxolane-4(R),5(R)-dicarboxylic acid N,N,N',N'-tetraethyl amide

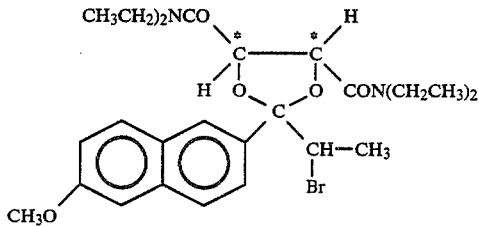

A mixture of the two diastereoisomers of 2-(1-bromoethyl)-2-(6-methoxy-2-naphthyl)-1,3-dioxolane-4(R),5(R)-dicarboxylic acid dimethyl ester 1 and 2 in ratio 1:2=1:1 (12.5 mmol; prepared as described in the example 1), diethylamine (27.5 ml) and of water (20 ml) was kept under stirring at room temperature for 15 hours. The solvents were removed at room temperature under reduced pressure and diethylether (50 ml) was added to the residue. The precipitate was filtered and dried in vacuo. A diastereoisomeric mixture of 2-(1-bromoethyl)-2-(6-methoxy-2-naphthyl)-1,3-dioxolane-4(R),5(R)-dicarboxylic acid N,N,N',N'-tetraethyl amide 13 and 14 (11 mmol; yield 88%) was obtained in ratio 13:14=1:1 (determined by $^1$H-NMR 200 MHz).

EXAMPLE 9

Preparation of the diastereoisomeric mixture of 2-(1-acetoxyethyl)-2-(5-bromo-6-methoxy-2-naphthyl)-1,3-dioxolane-4(R),5(R)-dicarboxylic acid dimethyl ester 2-Acetoxy-1,1-dimethoxy-1-(5-bromo-6-methoxy-2-naphthyl)-propane (1.22 g, 3.46 mmol) was added, under argon, to a solution obtained by heating at 65° C. a mixture of 2(R),3(R)-dihydroxybutanedioic acid dimethyl ester (20 g), thionyl chloride (1 ml) and methanesulfonic acid (0.03 g). The reaction mixture was heated at 95° C. for 30 minutes; then it was poured into a 10% aqueous solution of sodium bicarbonate and extracted with dichloromethane. The combined organic extracts were washed with water, dried over sodium sulphate, filtered, and concentrated in vacuo. Purification of the residue by column chromatography (silica gel, eluent dichloromethane: hexane=9:1) gave the diastereoisomeric mixture of 2-(1-acetoxyethyl)-2-(5-bromo-6-methoxy-2-naphthyl)-1,3-dioxolane-4(R),5(R)-dicarboxylic acid dimethyl ester 15 and 16 (0.7 g, 1.37 mmol; yield 40%) in ratio 15:16=65:35 (determined by $^1$H-NMR and HPLC). Crystallization from methanol gave a diastereoisomeric mixture in ratio 15:16=95:5.

$^1$H-NMr (90 MHz, CDCl$_3$-TMS), delta (ppm): Diastereoisomer 15 (major): 1.28(3H, d, J=6 Hz); 1.93(3H, s); 3.47(3H, s); 3.87(3H, s); 4.00(3H, s); 4.96(2H, ABq, Δγ=12.35, J=5.4 Hz); 5.38(1H, q, J=6 Hz); 7.23–8.30(5H, aromatic protons).

Diastereoisomer 16 (minor): 1.23(3H, d, J=6 Hz); 2.05(3H, s); 3.60(3H, s); 3.87(3Hs, s); 4.00(3H, s); 4.90(2H, ABq, Δγ=22.95, J=7 Hz); 5.38(1H, q, J=6 Hz); 7.23–8.30(5H, aromatic protons).

EXAMPLE 10

Preparation of the diastereoisomeric mixture of 2-(1-acetoxyethyl)-2-(6-methoxy-2-naphthyl)-1,3-dioxolane-4(R),5(R)-dicarboxylic acid dimethyl ester 2-Acetoxy-1,1-dimethoxy-1-(6-methoxy-2-naphthyl)-propane-(23.5 g, 73.8 mmol) was added, under argon, to a solution obtained by heating at 65° C. a mixture of 2(R),3(R)-dihydroxy-butanedioic acid dimethyl ester (150 g), thionyl chloride (15.6 ml) and methanesulfonic acid (0.7 g, 7.4 mmol). The reaction mixture was heated at 95° C. for 30 minutes; then it was poured into a 10% aqueous solution of sodium bicarbonate and extracted with dichloromethane. The combined organic extracts were washed with water, dried over sodium sulphate, filtered and concentrated in vacuo.

Purification of the residue by column chromatography (silica gel; eluent dichloromethane:hexane=7:3) gave the diastereoisomeric mixture of 2-(1-acetoxyethyl)-2-(6-methoxy-2-naphthyl)-1,3-dioxolane-4(R),5(R)-dicarboxylic acid dimethyl ester 17 and 18 (15 g, 34.7 mmol; yield 47%) in ratio 17:18=64:36 (determined by $^1$H-NMR and HPLC).

$^1$H-NMR (90 MHz, CDCl$_3$-TMS), delta (ppm): Diastereoisomer 17 (major): 1.23(3H, d, J=6 Hz); 1.95(3H, s); 3.45(3H, s); 3.83(3H, s); 3.88(3H, s); 4.90(2H, ABq, Δγ=6.82, J=5.4 Hz); 5.33(1H, q, J=6 Hz); 7.06–8.00(6H, aromatic protons).

Diastereoisomer 18 (minor): 1.20(3H, d, J=6 Hz); 2.00(3H, s); 3.57(3H, s); 3.81(3H, s); 3.88(3H, s); 4.80(2H, ABq, Δγ=15.54, J=6.6 Hz); 5.33(1H, q, J=6 Hz); 7.06–8.00(6H, aromatic protons).

EXAMPLE 11

Preparation of the diastereoisomeric mixture of 2-(1-hydroxyethyl)-2-(6-methoxy-2-naphthyl)-1,3-dioxolane-4(R),5(R)-dicarboxylic acid dimethyl ester A solution of a diastereoisomeric mixture of 2-(1-acetoxyethyl)-2-(6-methoxy-2-naphthyl)-1,3-dioxolane-4(R),5(R)-dicarboxylic acid dimethyl ester 17 and 18 in ratio 17:18=1:1 (4.33 g, 10 mmol) in methanol (20 ml), was added dropwise at room temperature to a solution of sodium hydroxyde (4 g, 100 mmol) in water (40 ml). The reaction mixture was kept at room temperature for 24 hours; then it was acidified with concentrated hydrochloric acid and extracted with diethylether. The combined organic extracts were washed with water, dried over sodium sulphate, and filtered. Evaporation of the solvent under reduced pressure gave the crude diastereoisomeric mixture of 2-(1-hydroxyethyl)-2-(6-methoxy-2-naphthyl)-1,3-dioxolane-4(R),5(R)-dicarboxylic acid (3.26 g).

The crude product, so obtained, was added to a solution of methanesulfonic acid (0.086 g, 0.9 mmol) in methanol (300 ml). The solution was heated at reflux for 2 hours, cooled at room temperature, diluted with dichloromethane (300 ml), and poured into water (100 ml). The organic phase was separated, washed with water and with a 2% aqueous solution of sodium bicarbonate, dried over sodium sulphate, and filtered. The reaction crude obtained by evaporation of the solvent under reduced pressure was crystallized from methanol to give the diastereoisomeric mixture of 2-(1-hydroxyethyl)-2-(6-methoxy-2-naphthyl)-1,3-dioxolane-4(R),5(R)-dicarboxylic acid dimethyl ester 19 and 20 (3 g, 7.7 mmol; yield 77%) in ratio 19:20=56:44 (determined by $^1$H-NMR and HPLC).

$^1$H-NMR (90 MHz, CDCl$_3$-TMS), delta (ppm): Diastereoisomer 19 (major): 1.06(3H, d, J=6 Hz); 3.13(1H, d, J=7.5 Hz); 3.30(3H, s); 3.83(3H, s); 3.90(3H, s); 4.16(1H, dq, J$_{CH-CH}$=6 Hz, J$_{CH-OH}$=7.5 Hz); 5.06(2H, ABq, $\Delta\gamma$=11.77, J=4.2 Hz); 7.13-8.00(6H, aromatic protons).

Diastereoisomer 20 (minor): 1.13(3H, d, J=6 Hz); 3.13(1H, d, J=7.5 Hz); 3.56(3H, s); 3.82(3H, s); 3.90(3H, s); 4.16(1H, dq, J$_{CH-CH}$=6 Hz, J$_{CH-OH}$=7.5 Hz); 4.97(2H, ABq, $\Delta\gamma$=2.94, J=1.5 Hz); 7.13-8.00 (6H, aromatic protons).

EXAMPLE 12

Preparation of the diastereoisomeric mixture of 2-[1-(4-methylphenylsulfonyloxy)-ethyl]-2-(6-methoxy-2-naphthyl)-1,3-dioxolane-4(R),5(R)-dicarboxylic acid dimethyl ester A solution of 1,1-dimethoxy-2-(4-methylphenylsulfonyloxy)-1-(6-methoxy-2-naphthyl)-propane (15 g, 34.8 mmol) in 1,2-dichlorethane (100 ml) was added dropwise, under argon, to a solution obtained by heating at 95° C. a mixture of 2(R),3(R)-dihydroxybutanedioic acid dimethyl ester (75 g), thionyl chloride (7.5 ml), and methanesulfonic acid (0.37 g, 3.8 mmol). The reaction mixture was heated at 125° C. for 1 hour and during this period 1,2-dichloroethane was distilled off.

The reaction mixture was then poured into a 10% aqueous solution of sodium bicarbonate and extracted with dichloromethane.

The combined organic extracts were washed with water, dried over sodium sulphate, filtered, and concentrated in vacuo.

Purification of the residue by column chromatography (silica gel; eluent dichloromethane:hexane=8:2) gave the diastereoisomeric mixture of 2-[1-(4-methylphenylsulfonyloxy)-ethyl]-2-(6-methoxy-2-naphthyl)-1,3-dioxolane-4(R),5(R)-dicarboxylic acid dimethyl ester 21 and 22 (10.8 g, 19.81 mmol; yield 57%) in ratio 21:22=40:60 (determined by $^1$H-NMR and HPLC).

$^1$H-NMR (200 MHz, CDCl$_3$-TMS), delta (ppm): Diastereoisomer 22 (major): 1.40(3H, d, J=6 Hz); 2.30(3H, s); 3.43(3H, s); 3.81(3H, s); 3.90(3H, s); 4.80(2H, s); 4.90(1H, q, J=6 Hz); 6.90-7.80(10H, aromatic protons).

Diastereoisomer 21 (minor): 1.37(3H, d, J=6 Hz); 2.26(3H, s); 3.43(3H, s); 3.83(3H, s); 4.76(2H, s); 4.90(1H, q, J=6 Hz); 6.90-7.80(10H, aromatic protons).

A further purification by column chromatography (silica gel; eluent dichloromethane:hexane=1:1) led to the pure major diastereoisomer 22.

EXAMPLE 13

Preparation of the diastereoisomeric mixture of 2-(1-methanesulfonyloxyethyl)-2-(6-methoxy-2-naphthyl)-1,3-dioxolane-4(R),5(R)-dicarboxylic acid dimethyl ester A solution of 1,1-dimethoxy-2-methanesulfonyloxy-1-(6-methoxy-2-naphthyl)-propane (24 g, 68 mmol) in 1,2-dichloroethane (140 ml) was added dropwise, under argon, to a solution obtained by heating at 95° C. a mixture of 2(R),3(R)-dihydroxy-butanedioic acid dimethyl ester (120 g), thionyl chloride (12 ml) and methanesulfonic acid (0.6 g, 7.4 mmol). The reaction mixture was heated at 125° C. for 1 hour and during this period 1,2-dichloroethane was distilled off. The reaction mixture was then poured into a 10% aqueous solution of sodium bicarbonate and extracted with dichloromethane. The combined organic extracts were washed with water, dried over sodium sulphate, filtered, and concentrated in vacuo.

Purification of the residue by column chromatography (silica gel; eluent dichloromethane:hexane=8:2) gave the diastereoisomeric mixture of 2-(1-methanesulfonyloxyethyl)-2-(6-methoxy-2-naphthyl)-1,3-dioxolane-4(R),5(R)-dicarboxylic acid dimethyl ester 23 and 24 (20 g, 42.7 mmol; yield 63%) in ratio 23:24=63:67 (determined by $^1$H-NMR and HPLC). Crystallization from methanol gave a diastereoisomeric mixture in ratio 23(RRS):24(RRR)=80:20.

$^1$H-NMr (90 MHz, CDCl$_3$-TMS), delta (ppm): Diastereoisomer 23 (RRS): 1.38(3H, d, J=6 Hz); 2.93(3H, s); 3.37(3H,. s); 3.90(3H, s); 4.80(1H, q, J=6 Hz); 5.03(2H, ABq, $\Delta\gamma$=5.09, J=4.2 Hz); 7.06-8.00(6H, aromatic protons).

Diastereoisomer 24(RRR): 1.38(3H, d, J=6 Hz); 2.93(3H, s); 3.53(3H, s); 3.80(3H, s); 3.90(3H, s); 4.80(1H, q, J=6 Hz); 4.97(2H, ABq, $\Delta\gamma$=11.94, J=6.3 Hz); 7.06-8.00(6H; aromatic protons).

EXAMPLE 14

Preparation of 2-(6-methoxy-2-naphthyl)-propanoic acid methyl ester from a diastereoisomeric mixture of 2-(1-methanesulfonyloxyethyl)-2-(6-methoxy-2-naphthyl)-1,3-dioxolane-4(R),5(R)-dicarboxylic acid dimethyl ester in ratio 80:20

The diastereoisomeric mixture of 2-(1-methanesulfonyloxyethyl)-2-(6-methoxy-2-naphthyl)-1,3-dioxolane-4(R),5(R)-dicarboxylic acid dimethyl ester 23 and 24 in ratio 23:24=80:20 (1 g, 2.13 mmol), methanol (7.5 ml), and water (2.5 ml) was heated in a sealed tube at 150° C. for 5 hours. The reaction mixture was cooled at room temperature, diluted with water, and extracted with diethylether. The combined organic extracts were washed with water, dried, filtered, and concentrated in vacuo.

Purification of the residue by column chromatography (silica gel; eluent dichloromethane) gave the 2-(6-methoxy-2-naphthyl)-propanoic acid methyl ester (0.4 g, 1.64 mmol; yield 77%).

M.p.=88° C.

$[\alpha]_D^{20}$=+48.02° (c=1%, chloroform).

$^1$H-NMR (200 MHz) analysis carried out in CDCl$_3$ using an optically active shift reagent (europium III tris-[3-(eptafluoropropylhydroxymethylene)-d-camphorate]) showed an enatiomeric ratio S(+):R(−)=80:20.

EXAMPLE 15

Preparation of 2-(6-methoxy-2-naphthyl)-propanoic acid from a diastereoisomeric mixture of 2-(1-bromoethyl)-2-(6-methoxy-2-naphthyl)-1,3-dioxolane-4(R),5(R)-dicarboxylic acid A mixture of the two diastereoisomers of 2-(1-bromoethyl)-2-(6-methoxy-2-naphthyl)-1,3-dioxolane-4(R),5(R)-dicarboxylic acid 5 and 6 in ratio 5:6=1:1 (12.75 g, 30 mmol) and of an aqueous solution (180 ml) prepared by dissolving K$_2$HPO$_4$ (26.1 g) and KH$_2$PO$_4$ (5.7 g) in water (384 ml) was heated, under stirring, at 100° C. for 21 hours. The reaction mixture was cooled at room temperature (pH 3.7) then was acidified with concentrated HCl to pH 1 and extracted with diethylether (3×100 ml). The combined organic extracts were washed with water and dried over sodium sulphate. Evaporation of solvent under reduced pressure gave the crude 2-(6-methoxy-2-naphthyl)-propanoic acid that was purified by column chromatography (silica gel; eluent hexane:diethylether=1:1).

The pure acid (4.83 g, 21 mmol; yield 70%) was obtained in 50% optical purity (enantiomeric excess).

M.p. 154°–155° C.

HPLC analysis, carried out as described in J. Pharm. Sci. 68, 112 (1979) showed an enantiomeric ratio S(+):R(−)=75:25.

The enantiomeric ratio was confirmed by $^1$H-NMR (200 MHz) analysis carried out as described in the example 14 on the corresponding methyl ester.

EXAMPLE 16

Preparation of 2-(6-methoxy-2-naphthyl)-propionic acid from 2-(1-bromoethyl)-2-(6-methoxy-2-naphthyl)-1,3-dioxolane-4(R),5(R)-dicarboxylic acid N,N,N',N'-tetraethyl amide A mixture of the two diastereoisomers of 2-(1-bromoethyl)-2-(6-methoxy-2-naphthyl)-1,3-dioxolane-4(R),5(R)-dicarboxylic acid N,N,N',N'-tetraethyl amide 13 and 14 in ratio 13:14=1:1 (1.07 g, 2 mmol) and of water (4 ml) was heated, under stirring, at 100° C. for 16 hours (acid pH). After work up as described in example 15 and purification by column chromatography (silica gel; eluent hexane:diethylether=1:1) pure 2-(6-methoxy-2-naphthyl)-propionic acid (0.124 g, 0.54 mmol; yield 27%) was obtained with 40% optical purity.

M.p. 154°–155° C.

$[\alpha]_D^{20} = +26.4°$ (c=1%, chloroform).

The enantiomeric ratio S(+):R(−)=70:30 was confirmed by HPLC and by $^1$H-NMR analysis carried out as described in example 15.

EXAMPLE 17

Preparation of 2-(6-methoxy-2-naphthyl)-propionic acid from 2-(1-chloroethyl)-2-(6-methoxy-2-naphthyl)-1,3-dioxolane-4(R),5(R)-dicarboxylic acid A mixture of the two diastereoisomers of 2-(1-chloroethyl)-2-(6-methoxy-2-naphthyl)-1,3-dioxolane-4(R),5(R)-dicarboxylic acid 9 and 10 in ratio 9:10=1:1 (24 mmol) and an aqueous solution (168 ml) of K$_2$HPO$_4$ (14.6 g) and KH$_2$PO$_4$ (3.19 g), having pH 6.6, was heated, under stirring, at 98° C. for 110 hours. The reaction mixture was cooled at room temperature (pH 5.7), acidified with concentrated HCl to pH 1 and extracted with diethylether (4×50 ml). The organic phase was extracted with a 10% aqueous solution of sodium bicarbonate (4×50 ml). The combined aqueous extracts were acidified to pH 1 and extracted with diethylether (4×90 ml). The combined organic phase was washed with water, dried over sodium sulphate and concentrated in vacuo.

The residue (4.8 g), 1,2-dimethoxyethane (72 ml) and concentrated HCl (36 ml) were heated, under stirring, at 75° C. for 2 hours. After work up of the reaction mixture as described in example 5 and purification by column chromatography (silica gel; eluent hexane:diethylether=7:3) pure 2-(6-methoxy-2-naphthyl)-propionic acid was obtained in 48% optical purity.

$[\alpha]_D^{20} = +31.6°$ (c=1%, chloroform).

The enantiomeric ratio S(+):R(−)=74:26 was confirmed by HPLC and by $^1$H-NMR analysis carried out as described in example 15.

EXAMPLE 18

A mixture of the two diastereoisomers of 2-(1-chloroethyl)-2-(6-methoxy-2-naphthyl)-1,3-dioxolane-4(R),5(R)-dicarboxylic acid 9 and 10 in ratio 9:10=1:1 (10 mmol) and of an aqueous solution (140 ml) of KH$_2$PO$_4$ (20 g) and sodium hydroxide (1 g), having pH 4.9 was heated at reflux for 240 hours.

The reaction mixture was cooled at room temperature (pH 3.6) and worked up as described in example 17.

Pure 2-(6-methoxy-2-naphthyl)-propionic acid was obtained in 62% optical purity.

$[\alpha]_D^{20} = +40.9°$ (c=1%, chloroform).

The enantiomeric ratio S(+):R(−)=81:19 was confirmed by HPLC and by $^1$H-NMR analysis carried out as described in example 15.

EXAMPLE 19

A mixture of the two diastereoisomers of 2-(1-bromoethyl)-2-(5-bromo-6-methoxy-2-naphthyl)-1,3-dioxolane-4(R),5(R)-dicarboxylic acid 25 and 26 in ratio 25:26=1:1 (2.52 g, 5 mmol; prepared as described in example 2 starting from diastereoisomers 11 and 12) and of an aqueous solution (70 ml) of KH$_2$PO$_4$ (10 g) and sodium hydroxide (1.4 g), having pH 6, was heated at 90° C. for 50 hours. The reaction mixture was cooled at room temperature (pH 5.9) and worked up as described in example 15.

Pure 2-(5-bromo-6-methoxy-2-naphthyl)-propionic acid (0.83 g, 2.7 mmol; yield 54%) was obtained in 70% optical purity.

M.p. 166°–168° C.

$[\alpha]_D^{20} = +29.4°$ C. (c=0.5%, chloroform).

The enantiomeric ratio S(+):R(−)=85:15 was confirmed by HPLC and by $^1$H-NMR analysis carried out as described in example 15.

EXAMPLE 20

A mixture of the two diastereoisomers of 2-(1-bromoethyl)-2-(5-bromo-6-methoxy-2-naphthyl)-1,3-dioxolane-4(R),5(R)-dicarboxylic acid 25 and 26 in ratio 25:26=1:1 (2.52 g, 5 mmol) and of an aqueous solution (70 ml) of KH$_2$PO$_4$ (10 g) and sodium hydroxide (0.5 g), having pH 5.15, was heated at 90° C. for 52 hours. The reaction mixture was cooled at room temperature (pH 4.40) and worked up as described in example 15.

Pure 2-(5-bromo-6-methoxy-2-naphtyl)-propionic acid (0.72 g, 2.33 mmol; yield 47%) was obtained in 68% optical purity.

M.p.=168°–170° C.

$[\alpha]_D^{20} = +28.8°$ (c=0.5%, chloroform).

The enantiomeric ratio S(+):R(−)=84:16 was confirmed by HPLC and by $^1$H-NMR analysis carried out as described in example 15.

EXAMPLE 21

Preparation of the diastereoisomeric mixture of 2(R)-hydroxy-3(R)-[2-(6-methoxy-2-naphthyl)-propanoyl]-butanedoic acid dimethyl ester A solution of triethylamine (4.45 g, 0.044 mol) in dichloromethane (10 ml) was added dropwise, at −10° C. in 5 minutes, to a mixture of 2(R),3(R)-dihydroxy-butanedioic acid dimethyl ester (44.5 g, 0.25 mol) and of dichloromethane (90 ml). To the mixture so obtained, a solution of 2-(6-methoxy-2-naphthyl)-propionyl chloride (5 g, 0.02 mol; prepared as described in Japanese Patent Application No. 57/145841, C.A. 98, 72492 h) in dichloromethane (25 ml) was added dropwise, at −10° C. in 20 minutes. The reaction mixture was poured into a 10% aqueous solution of sodium bicarbonate (200 ml), and extracted with dichloromethane (100 ml). The organic phase was washed with diluted HCl, with water, and dried over sodium sulphate. Evaporation of the solvent under reduced pressure, gave the crude diastereoisomeric mixture of 2(R)-hydroxy-3(R)-[2-(6-methoxy-2-naphthyl)-propanoyl]-butanoic acid dimethyl ester A and B (5.5 g) in ratio A:B=1:1 (determined by $^1$H-NMR).

$^1$H-NMR (200 MHz, CDCl$_3$-TMS), delta (ppm): all data are identical to those reported for diastereoisomers A and B in example 4. Crystallizations from methanol induced by pure crystalline diastereoisomer A gave the pure diastereoisomer A (RRS).

M.p.=77°–79° C.

$[\alpha]_D^{20} = +73.7°$ (c=1%, chloroform).

We claim:

1. Alkyl aryl-ketal having the formula

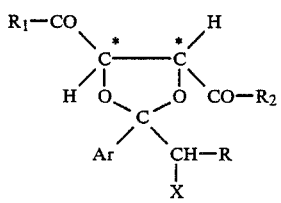

(I)

wherein

Ar represents naphthyl or naphthyl substituted by halogen, C$_1$–C$_4$ alkyl, C$_3$–C$_6$ cycloalkyl, benzyl, hydroxy, C$_1$–C$_4$ alkoxy, C$_1$–C$_4$ alkylthio, C$_1$–C$_4$ haloalkyl, C$_1$–C$_4$ haloalkoxy, phenoxy, thienylcarbonyl or benzoyl, R represents C$_1$–C$_4$ alkyl, R$_1$ and R$_2$ each independently represent hydroxy, O$^-$M$^+$, OR$_3$ or

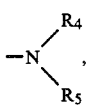

R$_3$ represents C$_1$–C$_24$ alkyl, C$_3$–C$_6$ cycloalkyl, phenyl or benzyl,

M$^+$ represents the cation of an alkaline metal,

R$_4$ and R$_5$, each independently, represent hydrogen, C$_1$–C$_4$ alkyl, C$_5$–C$_6$ cycloalkyl, (CH$_2$)$_n$—CH$_2$OH wherein n equals 1, 2 or 3, or R$_4$ and R$_5$ together represent (CH$_2$)$_m$ wherein m equals 4 or 5, or CH$_2$—CH$_2$—R$_6$—CH$_2$—CH$_2$ wherein R$_6$ represents O, NH or N—(C$_1$–C$_4$) alkyl, X represents chlorine, bromine, iodine, hydroxy, carboxylic acyloxy, alkylsulphonyloxy or arylsulphonyloxy, the carbon atoms marked by an asterisk being both contemporaneously in the R or S configuration.

2. The alkyl aryl-ketal of claim 1 wherein the substituted naphthyl is selected from the group consisting of 6-methoxy-2-naphthyl, 5-chloro-6-methoxy-2-naphthyl, 5-bromo-6-methoxy-2-naphthyl, 6-hydroxy-2-naphthyl, 5-bromo-6-hydroxy-2-naphthyl and 5-chloro-6-hydroxy-2-naphthyl.

3. The alkyl aryl-ketal of claim 1 wherein when X is carboxylic acyloxy, X is selected from the group consisting of acetoxy, trifluoroacetoxy, trichloroacetoxy, benzoyloxy and 4-nitrobenzoyloxy.

4. The alkyl aryl-ketal of claim 1 wherein, when X is alkylsulphonyloxy, X is mesyloxy.

5. The alkyl aryl-ketal of claim 1 wherein when X is arylsulphonyloxy, X is selected from the group consisting of benzene sulphonyloxy and tosyloxy.

6. Alkyl aryl-ketal having the formula

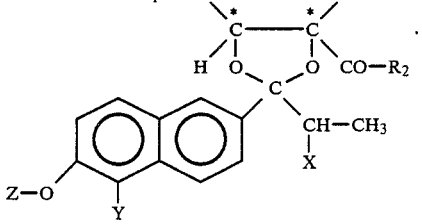

(IV)

wherein

R$_1$ and R$_2$ each independently represent hydroxy, O$^-$M$^+$, OR$_3$ or

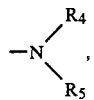

R$_3$ represents C$_1$–C$_{24}$ alkyl, C$_3$–C$_6$ cycloalkyl, phenyl or benzyl, M$^+$ represents the cation of an alkaline metal, R$_4$ and R$_5$, each independently, represent hydrogen, C$_1$–C$_4$ alkyl, C$_5$–C$_6$ cycloalkyl, (CH$_2$)$_n$—CH$_2$OH wherein n equals 1, 2 or 3, or R$_4$ and R$_5$ together represent (CH$_2$)$_m$ wherein m equals 4 or 5, or CH$_2$—CH$_2$—R$_6$—CH$_2$—CH$_2$ wherein R$_6$ represents O, NH or N—(C$_1$–C$_4$) alkyl, X represents chlorine, bromine, iodine, hydroxy, carboxylic acyloxy, alkylsulphonyloxy or arylsulphonyloxy, Z represents hydrogen, methyl or alkaline metal, and Y is hydrogen, chlorine or bromine, the carbon atoms marked by an asterisk being both in configuration R or S.

7. Alkyl aryl-ketal of the formula

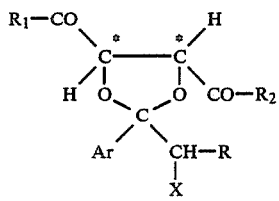 (I)

wherein

Ar represents naphthyl, 6-methoxy-2-naphthyl, 5-chloro-6-methoxy-2-naphthyl, 5-bromo-6-methoxy-2-naphthyl, 6-hydroxy-2-naphthyl, 5-bromo-6-hydroxy-2-naphthyl and 5-chloro-6-hydroxy-2-naphthyl, R represents $C_1$–$C_4$ alkyl, $R_1$ and $R_2$ each independently represent hydroxy, $O^-M^+$, $OR_3$ or

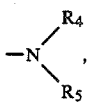, $R_3$ represents $C_1$–$C_{24}$ alkyl, $C_3$–$C_6$ cycloalkyl, phenyl or benzyl, $M^+$ represents the cation of an alkaline metal, $R_4$ and $R_5$, each independently, represent hydrogen, $C_1$–$C_4$ alkyl, $C_5$–$C_6$ cycloalkyl, $(CH_2)_n$—$CH_2OH$ wherein n equals 1, 2 or 3, or $R_4$ and $R_5$ together represent $(CH_2)_m$ wherein m equals 4 or 5, or $CH_2$—$CH_2$—$R_6$—$CH_2$—$CH_2$ wherein $R_6$ represents O, NH or N—($C_1$–$C_4$) alkyl, X represents chlorine, bromine, iodine, hydroxy, acetoxy, trichloroacetoxy, trifluoroacetoxy, benzoyloxy, 4-nitrobenzoyloxy or —O—$SO_2$—$R_7$ wherein $R_6$ represents —$CH_3$, —$C_6H_5$ or —$C_6H_4$—$CH_3$, the carbon atoms marked by an asterisk being both contemporaneously in the R or S configuration.

* * * * *